United States Patent [19]

Nuwayser

[11] Patent Number: 5,648,097

[45] Date of Patent: Jul. 15, 1997

[54] CALCIUM MINERAL-BASED MICROPARTICLES AND METHOD FOR THE PRODUCTION THEREOF

[75] Inventor: Elie S. Nuwayser, Wellesley, Mass.

[73] Assignee: Biotek, Inc., Woburn, Mass.

[21] Appl. No.: 538,635

[22] Filed: Oct. 4, 1995

[51] Int. Cl.$^6$ .......................... A61K 9/16; A61K 47/04; A01N 25/12

[52] U.S. Cl. .......................... 424/489; 424/490; 424/426; 424/421; 424/602; 424/696; 428/402; 428/402.24; 428/403; 264/5; 264/7; 514/952; 71/64.13; 71/DIG. 1

[58] Field of Search .......................... 424/426, 489, 424/490, 602, 696; 428/402, 402.24, 403; 264/5, 7

[56] References Cited

U.S. PATENT DOCUMENTS

| | | | |
|---|---|---|---|
| 4,101,501 | 7/1978 | Hinterwaldner | 523/210 |
| 4,448,599 | 5/1984 | Mackenzie et al. | 65/21.4 |
| 4,518,547 | 5/1985 | Cuff et al. | 424/497 |
| 4,568,559 | 2/1986 | Nuwayser et al. | 427/3 |
| 4,612,053 | 9/1986 | Brown et al. | 706/35 |
| 4,623,588 | 11/1986 | Nuwayser et al. | 428/402 |
| 4,880,610 | 11/1989 | Constantz | 423/305 |
| 5,053,212 | 10/1991 | Constantz et al. | 423/305 |
| 5,178,845 | 1/1993 | Constantz et al. | 423/305 |
| 5,336,264 | 8/1994 | Constantz et al. | 623/16 |

OTHER PUBLICATIONS

Influences of Matrixes on Nylon–Encapsulated Pharmaceuticals; McGinty, et al., Journal of Pharmaceutical Sciences, vol. 70, No. 4, Apr. 1981, pp. 372–375.

Effect of formulation factors on the matrix pH of nylon microcapsules; Cuff, et al., J. Microencapsulation, 1984, vol. 1, No. 27–32.

Coral Chemistry Leads to Human Bone Repair; Pool, Robert;Science, vol. 267, Mar. 1995, p. 1772.

Skeletal Repair by in Situ Formation of the Mineral Phase of Bone; Constantz, et al., Science, vol. 267, Mar. 1995.

Response of Oral Tissues to Implants Totally Covered by Mucous Membrane; Weinberg, S. and Moncarz, V., Oral Science Review, 1974, vol. 5, pp. 68–84.

Sustained Release Injectable Naltrexone Microcapsules; Nuwayser, et al., Proceed. Intern. Symp. Control. Rel. Bioact. Mater., 15 (1988), No. 119.

Sustained Release Injectable Methadone Microcapsules; Nuwayser, et al., Proceed. Intern. Symp. Control. Rel. Bioact. Mater., 16 (1989), No. 29.

Polyanhydride Microspheres as Drug Carriers I. Hot–Melt Microencapsulation; Mathiowitz, E. and Langer, R., Journal of Controlled Release, 5 (1987) 13–22.

Plaster of Paris: Thermal Properties and Biocompatibility; Högset, O. and Bredberg, G., Acta Otolaryngol (Stockh) 1986; 101: 445–452.

The Use of Plaster of Paris to Fill Large Defects in Bone; Peltier, L., American Journal of Surgery, vol. 97, Mar. 1959, pp. 311–315.

Use of alloplastics for ridge augmentation; Topazian, R., et al., J Oral Surgery, vol., 29, Nov. 1971, pp. 792–798.

Biodegradable Poly(lactic acid) Polymers; Kulkarni, R.K., et al., J. Biomed. Mater. Res., vol. 5, pp. 169–181 (1971).

(List continued on next page.)

Primary Examiner—Edward J. Webman
Attorney, Agent, or Firm—Banner & Witcoff, Ltd.

[57] ABSTRACT

A novel method of producing biodegradable microparticles is disclosed. Inorganic calcium salts are mixed with water to form a slurry. The slurry is then added to an oil bath which is then mixed to form an emulsion. The mixing continues for a period of time sufficient to form hardened microparticles. The hardened microparticles are then retrieved and characterized. Biologically active agents may be added to the slurry prior to emulsification, or they may be added to the hardened microparticles after production. The microparticles may be injected into a human being whereby they act as controlled release drug delivery vehicles.

14 Claims, 2 Drawing Sheets

OTHER PUBLICATIONS

Plasma Levels of Tegafur Following Implantation of Polycarbonate Pellets Containing Tegafur or FD-1 into Rats; Kawaguchi, T., Chem. Phar.Bull., No. 11, pp. 4157–4160.

Materials and Biological Aspects of Synthetic Polymers in Controlled Drug Systems: Problems and Challenges; Bruck, S., et al., CRC Critical Reviews in Therapeutic Drug Carrier Systems, vol. 5, Issue 3.

More about the degradation of LA/GA–derived matrices in aqueous media; Vert, M., Journal of Controlled Release, 16, (1991) 15–16.

Biodegradable Drug Delivery Systems; Wood, David A., International Journal of Pharmaceutics, 7 (1980) 1–18.

Polybutylcyanoacrylate nanoparticles for the delivery of [$^{75}$Se]norcholestenol], Kreuter, J. et al., International journal of Pharmaceutics, 16 (1983) 105–113.

Use of heterogenous bone in oral surgery; J. Oral Surgery., vol. 19, Nov. 1961, No. 6, pp. 459–474.

Microencapsulation with Microfluidized Beds; Proceed. Intern. Symp. Control Rel. Bioact. Mater., 14 (1987), Controlled Release Society, pp. 304–305.

Microencapsulation of Contraceptive Steroids; Nuwayser, E. et al., Long Acting Contraceptive Delivery Systems, G.I. Zatuchni, et al., eds. Harper & Row, (1984) pp. 64–76.

FIG.1

CALCIUM MINERAL-BASED MICROPARTICLES AND METHOD FOR THE PRODUCTION THEREOF

BACKGROUND OF THE INVENTION

1. Field of the Invention

Embodiments of the present invention relate generally to mineral based microparticles and methods for the production thereof. Embodiments of the present invention relate further to novel biodegradable and/or bioerodible microparticles having as a major component an inorganic calcium compound. Embodiments of the present invention also relate to methods of producing such microparticles by using a novel emulsion technique. The microparticles are useful in the controlled delivery of desired agents, such as biologically active agents and, given their biocompatability, are useful as injectable or implantable drug delivery vehicles. Embodiments of the present invention also relate to novel controlled drug delivery vehicles produced by coating such mineral based microparticles with a polymer, mineral or lipid shell to produce microcapsules.

2. Description of Related Art

A variety of methods to produce biodegradable drug delivery systems exist. For example, biodegradable polymer systems exist which include polylactide-co-glycolides, polycarbonates, polyalkylcyanoacrylates, and polyanhydrides. Biodegradable polymer systems have been investigated for their in vivo drug delivery capability as implants, microspheres, microcapsules, nanoparticles, aggregates, and micelles. These biodegradable polymers have been developed into useful products, and have been the subject of many review articles.

As useful as biodegradable polymers are, they have proven difficult to develop into practical parenteral systems, in part because they release drugs by a complex combination of mechanisms including homogeneous hydrolysis, enzymatic hydrolysis, diffusion, percolation, and matrix degradation. For example, the release of drugs from polylactide-co-glycolide microspheres typically involves an early burst, presumably because drug near the surface dissolves quickly, and a late burst produced after the polymer lattice has degraded sufficiently to allow more deeply confined drug to escape. Although complex polymeric media have been developed into promising biodegradable delivery systems, there remains a real need for alternative matrices which have a simpler release mechanism and which lead more readily to uniform rates of drug delivery. Such delivery systems should be biocompatible, chemically inert, cleanly resorbable, easily made, easily injectable or implantable and readily able to be coated with compounds designed to alter degradation and delivery of a biologically active agent.

Calcium sulfates have been proposed in forming matrices in non biodegradable nylon microcapsules using an emulsion interfacial polymerization technique. See, McGinity et al. *J. Poly. Sci.*, Vol. 70, page 372 (1981); Cuff et al. *J. Microencapsulation*, Vol. 1, page 27 (1984). Calcium phosphates, including hydroxyapatite and carbonated hydroxyapatite have been proposed for dental and bone cements. See, Brown et al. U.S. Pat. No. 4,612,053, and U.S. Pat. Nos. 5,053,212, 5,178,845, 5,336,264, and 4,880,610 to Constantz. Similarly, calcium sulfates have been proposed as bone cements. See, Peltier et al., *American Journal of Surgery*, Vol. 97, pages 311–315, March 1959. These references, however, fail to provide biodegradable mineral based microparticles or an advantageous method for their production.

SUMMARY OF THE INVENTION

Embodiments of the present invention are directed to mineral microparticles, and more particularly, to novel microparticles which have as their major component an inorganic salt of calcium. Embodiments of the present invention are further directed to novel methods for producing microparticles by mixing an inorganic salt of calcium with water to form a slurry, emulsifying the slurry in a viscous organic continuous phase until hardened microparticles having an exposed surface of the inorganic calcium salt develop, and then retrieving the microparticles.

The microparticles as described herein are generally uniform in shape and, more preferably, substantially spherical particles ranging in size from one micron to several millimeters in diameter and are distinguishable from ground powders which are generally non-uniform in shape and are generally non-spherical. The microparticles are injectable by a standard syringe or can be implanted by a trochar. The term "microparticles" as used herein is intended to include microspheres which are generally characterized as substantially spherical microparticles. The term "hydroformed" as it relates to the microparticles of the present invention refers to microparticles formed from an emulsion of an aqueous slurry of an inorganic salt in a viscous organic continuous phase.

The novel microparticles of the present invention can be loaded with a biologically active agent and are useful as injectable (parenteral) or implantable, bioerodible delivery systems. After formation and retrieval of the novel microparticles, the exposed surface of the inorganic calcium salt can be coated with a biologically acceptable and biodegradable and/or bioerodible material to produce a microcapsule having a drug delivery profile which is different from the microparticles themselves. Thus both the microparticles and the microcapsules of the present invention are completely biodegradable and/or bioerodible. Once implanted into the human body, they can completely biodegrade and/or bioerode thereby advantageously leaving no non biodegradable and/or non bioerodible component.

The novel microparticles of the present invention are also useful where delivery of an active ingredient is desired, and where the appropriate conditions for the erosion or degradation of the microparticles exists. For example, use of the mineral based microparticles for the delivery of active ingredients, such as fertilizers, insecticides, paraticides and the like or the inorganic salts themselves for agricultural use, to soils represents an alternate and advantageous embodiment of the present invention.

It is accordingly an object of the present invention to provide delivery systems based on mineral microparticles. It is a further object of the present invention to develop novel mineral microparticles which are capable of degrading or eroding in a simple manner. It is yet an even further object of the present invention to provide mineral based microparticles which are biocompatible, chemically inert, cleanly resorbable, and easily made. It is yet a still further object of the present invention to provide mineral based microparticles which can be readily coated with compounds designed to alter delivery rates of an active ingredient. It is yet a still further object of the present invention to provide a novel method of making biodegradable and/or bioerodible microparticles by mixing an inorganic salt of calcium with water to form a slurry, emulsifying the slurry in oil until hardened microparticles develop, and then retrieving the microparticles.

Other objects, features or advantages of the present invention will become apparent from the following description taken in conjunction with the accompanying drawings.

BRIEF DESCRIPTION OF THE DRAWINGS

In the course of the detailed description of certain preferred embodiments to follow, reference will be made to the attached drawings, in which.

DETAILED DESCRIPTION OF CERTAIN PREFERRED EMBODIMENTS

Figure 1:
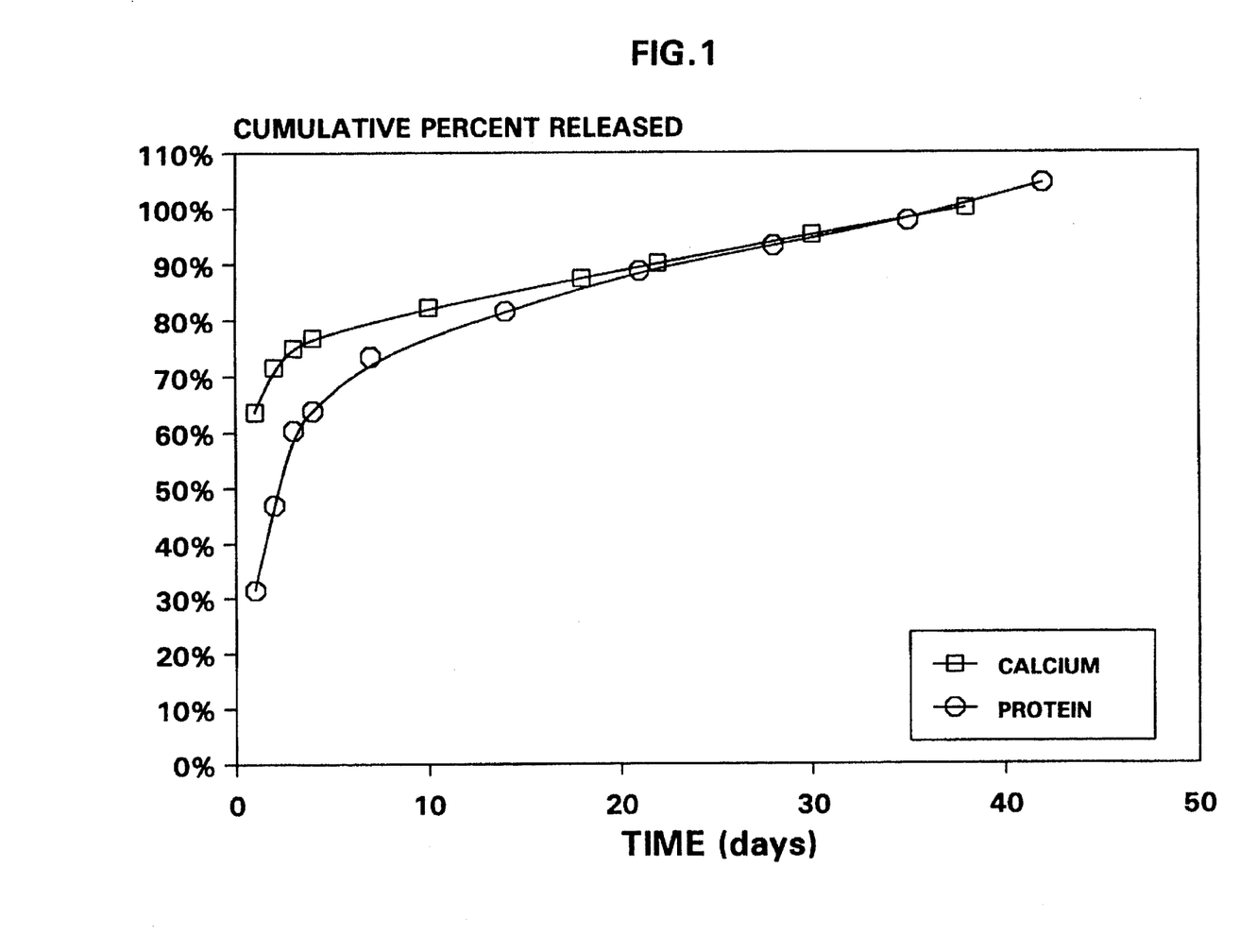
FIG. 1 is a graph showing percentage release of bovine serum albumin over a 3 week period.
Figure 2:
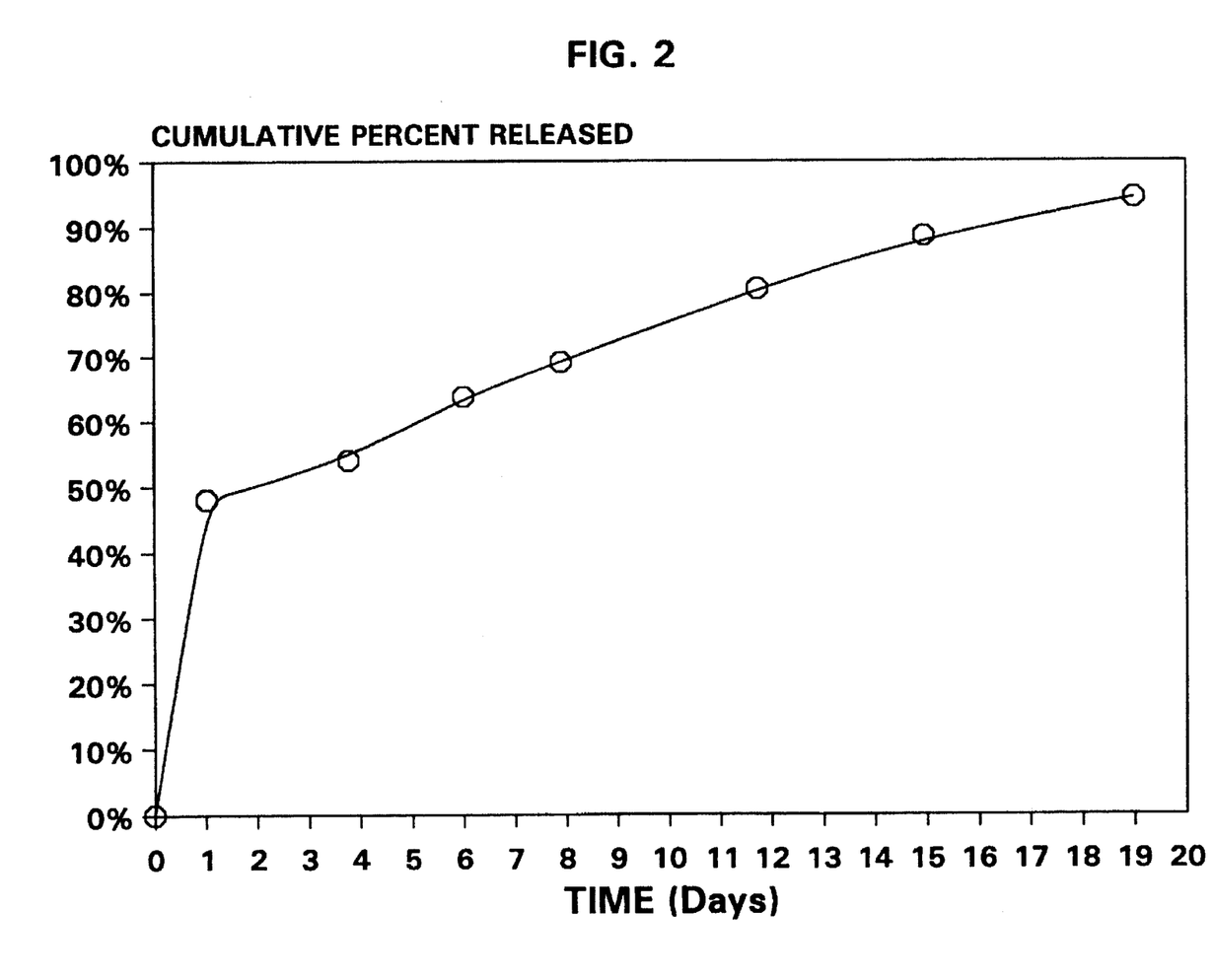
FIG. 2 is a graph showing percent release of calcium ion and protein enzyme from calcium sulfate microparticles encapsulated by suppository wax.

The novel microparticles of the present invention are mineral based, i.e. a major component of the novel microparticles is a biocompatible inorganic salt. In a preferred embodiment, the major component of the novel microparticles is an inorganic salt of calcium which hardens after slurrying with water. The novel microparticles are preferably injectable and may also contain active ingredients, surfactants, fillers, inert materials and the like. In addition to being biocompatible, the inorganic salts of calcium are desirable because they are chemically inert within the human body and are readily commercially available and, in many cases, are capable of hardening after admixture with water.

According to the teachings of the present invention, the novel microparticles may be easily, though surprisingly, prepared through a novel emulsion technique referred to herein as "hydroforming". In a principal aspect, an anhydrous or incompletely hydrated inorganic salt of calcium, or a mixture of such salts, in the form of a powder is mixed with water or an aqueous solution to form an inorganic calcium salt slurry. It is frequently observed that such slurries will then spontaneously harden into a solid mass through chemical and/or physical pathways if no further action is taken. Before hardening, however, the slurry is introduced into a stirred bath containing a viscous liquid, such as corn oil, whereupon the slurry is emulsified into discrete inorganic calcium salt slurry particles. The emulsion is stirred until hardened microparticles develop having an exposed surface of the inorganic calcium salt, which are then retrieved and characterized by microparticle size and porosity. The inorganic calcium salt component of the microparticles is in direct contact with the viscous liquid during the formation and hardening process. The method of the present invention produces large quantities of completely biodegradable and/or bioerodible microparticles ranging in size from a one micron to more than a few thousand microns in diameter in an easy, efficient and cost effective manner.

The microparticles are characterized as being substantially uniform in shape, and preferably substantially spherical, and having a substantially smooth surface. The microparticles of the present invention are distinguishable from ground powders in that ground powders are generally non-uniform in shape and are generally non-spherical. Ground powders are further characterized as having rough, irregular surfaces indicating breakage of the crystal structure of the substrate being ground due to the uncontrolled nature of the grinding process to produce the particular powder.

Due to their consistent uniform shape and/or smooth surface, the microparticles of the present invention are less prone to clogging and advantageously provide smooth flow characteristics upon delivery from a syringe needle, which is a significant injection performance advantage, when compared to ground powders in injectable formulations. The smooth flow characteristics enable a greater amount of microparticles to be injected when compared to formulations using ground powders, and therefore, injectable microparticle formulations enable the delivery of a greater amount of active ingredient per injection.

In the practice of the present invention, an injectable formulation is made by mixing a desired amount of the microparticles according to the present invention with a suitable commercially available suspending medium to produce a suspension. A desired volume of the suspension is then drawn into a syringe and injected into a patient.

The microparticles of the present invention may be loaded with an active ingredient such as a biologically active agent or an active agent useful in agriculture by introducing the active ingredient into the slurry prior to formation of the microparticles, or, alternatively, by impregnating the microparticles with the active ingredient after microparticle formation, hardening, and retrieval. After microparticle formation, hardening, and retrieval, the novel microparticles may then be coated with a biodegradable and/or bioerodible compound using techniques known to those skilled in the art to alter degradation and the delivery profile of the active ingredient. Such microparticles are said to be microencapsulated and are referred to herein as "microcapsules".

According to certain embodiments of the present invention, mineral microparticles can be produced having certain physical characteristics useful for bioerodible delivery systems, including desirable solubilities and porosities for long term delivery. According to certain embodiments of the present invention, microparticles can be tailored to achieve delivery of a steady and constant amount of an active ingredient for a period of days to weeks to months through a single parenteral injection.

The starting materials useful in preparing the microparticles of the present invention include sulfates, phosphates and silicates of calcium, whether alone or as a mixture. Sparingly soluble calcium minerals are especially suitable for injectable drug delivery systems because they completely erode in an aqueous environment by a simple process in which their exposed surface gradually dissolves away. The erosion of the mineral microparticle results in a very desirable mechanism for achieving uniform drug delivery, unlike polymer based systems. The inorganic minerals useful in the present invention are further advantageous in that they do not form complex by-products after they erode. Instead they simply and completely dissolve into their constituent ions by physical rather than chemical processes, and tend to be well tolerated in the body.

Examples of specific useful calcium compounds include gypsum ($CaSO_4 \cdot 2H_2O$), which is made from plaster of Paris ($CaSO_4 \cdot .5H_2O$); hydroxyapatite ($Ca_5(PO_4)_3OH$), made by nucleated recrystallization of a mixture of $Ca_4(PO_4)_2O$ and $Ca(HPO_4) \cdot 2H_2O$; and hydrated calcium silicates which are made from water and a calcined mixture of $CaSiO_3$ and $Ca_2SiO_4$ resembling Portland cement. Other inorganic compounds with the ability to harden in water are also useful in the practice of the present invention whether as injectable microparticles or as microparticle delivery systems for fertilizers or other active agents. Accordingly, based on the teachings of the present invention, one of ordinary skill in the art will be able to identify additional inorganic mineral salts and mixtures thereof useful in the preparation of the microparticles of the present invention.

Calcium sulfate compounds are useful in the practice of certain embodiments of the present invention. They occur naturally as anhydrite, $CaSO_4$, also called karstenite; and as gypsum $CaSO_4.2H_2O$, also referred to as alabaster. Plaster of Paris is prepared from powdered gypsum by heating at 100° C.–160° C. producing a fine white powder. When mixed with 0.2 to 1.0 parts of water, plaster of Paris forms a smooth, creamy slurry which sets in a matter of minutes to a hard, somewhat porous mass of microscopic $CaSO_4.2H_2O$ crystals. The degree of internal porosity in plaster of Paris can range from about 35% to about 50%, depending primarily on the water-to-plaster ratio used. Plaster of Paris is a simple, inexpensive, stable and readily available substance which has been investigated for implant material and found to be biologically inert. It is easily sterilizable and well tolerated by both hard and soft tissue. It does not stimulate chronic inflammatory cell or foreign body giant cell activity and serum calcium levels are not altered by implanted plaster.

Calcium phosphate compounds are also useful in the practice of certain embodiments of the present invention. There are many sparingly soluble calcium phosphates useful in the present invention which are stable at room temperature, including $CaHPO_4$, $CaHPO_4.2H_2O$, both the alpha and beta $Ca_3(PO_4)_2$, $Ca_2H_2(PO_4)_2O$, and also $Ca_5(PO_4)_3OH$ and the like. Among these calcium phosphate compounds, $Ca_5(PO_4)_3OH$, otherwise known as hydroxyapatite, is the chief mineral constituent of bone and teeth, and it can be made by the nucleated recrystallization of a mixture of $Ca_4(PO_4)_2O$ and $CaHPO_4.2H_2O$ in the presence of water.

Calcium phosphate biomaterials have been prepared and investigated in a number of forms, the most widely studied being tricalcium phosphate and hydroxyapatite used as bioresorbable bone scaffolding. The calcium phosphates are particularly useful due to their complete biocompatability. No foreign body reactions, local inflammatory response, or systemic toxicity have been reported, and studies have shown that calcium and phosphate ions introduced as part of implanted minerals are handled by the body as part of the normal ion pool.

Calcium silicates, also useful in the practice of the present invention, take the form of hydrated calcium silicates made from water and a calcined mixture of various mixtures of neutral calcium silicates such as $CaSiO_3$ and $Ca_2SiO_4$, resembling Portland cement. During the cure of microparticles, however, the particular calcium silicate employed may render the microparticles too alkaline to be physiologically or pharmaceutically acceptable. In order to render the microparticles useful as an injectable drug delivery vehicle, excess base may be leached out of the cured microparticles after they have been made, forming neutral microparticles suitable for impregnation with biologically active agents for parenteral use.

The microparticles of the present invention can be advantageously tailored to have different erosion lifetimes by employing combinations of inorganic salts, calcium or otherwise, having differing solubilities and hydration behavior, as well as, different salt to water ratios. In addition, setting retardants, such as acetone, can be added to the water prior to making the slurry microparticles. The setting retardants increase the setting or hardening time of the microparticles thereby allowing the microparticles to develop more complex and uniform crystal structures. The result is a microparticle which takes longer to dissolve in aqueous media thereby extending the erosion lifetime of the microparticle. Other constituents such as pharmaceutical excipients including dextran, lactose, glucose, gums and the like which are routinely used in tablet making, and other pharmaceutical preparations and biologically active agents which may optionally be present in the microparticles can also be used to effect the erosion rate. In addition, microparticle size can be regulated to achieve a wide range of erosion rates.

The term "drug" or "biologically active agent" as used herein includes without limitation physiologically or pharmacologically active substances that act locally or systemically in the body. Representative drugs and biologically active agents to be used with the microparticles of the present invention include, without limitation, peptide drugs, protein drugs, desensitizing agents, antigens, vaccines, anti-infectives, antibiotics, antimicrobials, antiallergenics, steroidal anti-inflammatory agents, decongestants, miotics, anticholinergics, sympathomimetics, sedatives, hypnotics, psychic energizers, tranquilizers, androgenic steroids, estrogens, progestational agents, humoral agents, prostaglandins, analgesics, antispasmodics, antimalarials, antihistamines, cardioactive agents, non-steroidal anti-inflammatory agents, antiparkinsonian agents, antihypertensive agents, β-adrenergic blocking agents, nutritional agents, and the benzophenanthridine alkaloids. To those skilled in the art, other drugs or biologically active agents that can be released in an aqueous environment can be utilized in the described delivery systems. Also, various forms of the drugs or biologically active agents may be used. These include, without limitation, forms such as uncharged molecules, molecular complexes, salts, ethers, esters, amides, etc., which are biologically activated when injected into the body.

The amount of drug or biologically active agent incorporated into the microparticles depends upon the inorganic mineral used, the desired release profile, the concentration of drug required for a biological effect, and the length of time that the drug has to be released for treatment. The lower limit of drug incorporated into the microparticles is dependent simply upon the activity of the drug and the length of time needed for treatment. Preferably, a sufficient amount of the active agent is loaded into the microparticles so as to produce a dose amount of the microparticles which may be therapeutically useful.

The following examples are set forth as representative of the present invention. These examples are not to be construed as limiting the scope of the invention as these and other equivalent embodiments will be apparent in view of the present disclosure, figures, tables, and accompanying claims.

EXAMPLE I

Hydroformed Calcium Sulfate Microparticles

Microparticles useful as injectable or implantable drug delivery systems have been prepared according to the following technique.

Preparation of Calcium Sulfate Hemi-hydrate (Plaster of Paris)

Since commercially available calcium sulfate hemihydrate (plaster of Paris) may vary in composition, it was prepared fresh prior to use in the practice of the present invention. Plaster of Paris was prepared by heating calcium sulfate dihydrate (Sigma Chemical No. C-3771) in a ventilated oven at 130 ° C. for four hours. The observed loss in weight equaled or slightly exceeded that predicted for conversion of calcium sulfate dihydrate to hemihydrate, and the weight gain on rehydration is consistent with the reverse conversion.

Preparation of Hydroformed Microparticles

In a typical preparation of hydroformed microparticles (batch 1), 5 grams of plaster of Paris was mixed in powdered form with 5 mls of water to form a slurry. The slurry was then immediately poured into a beaker containing 400 ml of corn oil at room temperature. The beaker was outfitted with a high shear mixer which was operated at 1200 RPM. The slurry-oil mixture was blended for a few seconds to form an emulsion. The emulsion was further blended for an additional 60 minutes until a suspension of hardened microparticles was formed. The calcium sulfate microparticles were characterized by having an exposed surface of calcium sulfate. The microparticles were in direct contact with the corn oil during formation and hardening of the microparticles. The stirrer was then turned off and the microparticles were collected by filtration. The microparticles were rinsed using ethyl acetate to remove the vegetable oil remaining in the porous microparticles, and air dried at 22° C. for at least 2 hours to remove any water.

Two other batches of calcium sulfate microparticles were prepared in a similar manner, however the composition of the liquid component was varied to include a liquid agent to retard or slow the setting time of the slurry. Specifically, in batch 2, the liquid added to the calcium sulfate was 0.5 ml of acetone as a setting retardant plus 4.5 ml water, and in batch 3, the liquid added to the calcium sulfate was 5 ml acetone as a setting retardant plus 5 ml of water.

Characterization of Microparticle Size Distribution

After collection, the hardened microparticles were passed through a series of sieves with decreasing mesh size to determine microparticle size distribution. An Allen-Bradley sonic sifter was used to ensure complete separation of microparticles.

Scanning Electron Microscopy (SEM)

Scanning Electron Microscopy (SEM) was utilized to examine the surfaces of the microparticles at magnifications of up to 300X. SEM revealed that microparticles produced as described above were generally uniform in shape, and preferably, spherical in shape and having a generally smooth surface of exposed calcium sulfate.

Visual Measurement of Dissolution Time

A visual dissolution study was conducted on microparticles produced according to the above method. The microparticles having exposed calcium sulfate surfaces that were made from a water or water/acetone slurry were placed in contact with distilled water. The dissolution of the microparticles was observed for six days at room temperature.

Results

The compositions of the microparticles and the results are summarized in Table 1 below.

| Batch # | CaSO$_4$ (g) | Water (ml) | Acetone (ml) | %<105 μm | %>105 μm | %53–150 μm | Dissolution Time (days) |
|---|---|---|---|---|---|---|---|
| 1 | 5 | 5 | 0.0 | 4 | 96 | 15 | 2 |
| 2 | 5 | 4.5 | 0.5 | 3 | 97 | 10 | 6 |
| 3 | 5 | 5 | 5 | 9 | 91 | 13 | 2.5 |

The sieve analysis revealed that microparticles between 5 to 500 microns in diameter resulted from the process of Example I. The size distribution did not vary significantly when the acetone was added. The microparticles were spherical in shape, and comprised of crystals of calcium salt.

Sample microparticles were deliberately broken open under a scanning electron microscope to reveal a clearly visible microcrystalline structure of cured plaster.

The microparticles prepared with water as the only suspending medium completely dissolved after two days. The microparticles prepared with a 10% acetone/water mixture took the longest to dissolve (six days), which is consistent with acetone being a setting retardant, since the slowed setting produced a microparticle structure with more density and crystalline strength, which in turn results in an increased dissolution time. Adding an excess of acetone in batch 3, however, did not increase the ability of acetone to act as a setting retardant, as the excess acetone only slightly increased the dissolution time over batch 1 which contained no acetone.

EXAMPLE II

Effects of the Viscosity of the Oil Continuous Phase on the Formation of Hydroformed Calcium Sulfate Microparticles The effect of the viscosity of oils and/or solvents used as the continuous phase into which the calcium salt slurry is placed was studied to determine the optimum conditions for preparing microparticles according to the method invention. The following continuous phase liquids were chosen because of their differing viscosities and because they are immiscible with water, however, it is to be understood that other continuous organic phase liquids, such as mineral oils and the like, can be employed in the practice of the present invention provided that they are substantially immiscible with water, have a viscosity which promotes the formation of useful microparticles and are non reactive with the particular calcium salt or other ingredients of the slurry:

1. Methylene chloride—an extremely hydrophobic chlorinated hydrocarbon of molecular weight 85. ($\eta$=approximately 1 centipoise).
2. Isopropylmyristate—a mixture of fatty acid esters of propane-2-ol of molecular weight 271 ($\eta$=approximately 10.6 centipoise); and
3. Corn oil—a mixture of various fatty acid esters of glycerol of molecular weight greater than 600 ($\eta$=approximately 60 centipoise at room temperature and $\eta$=approximately 25 centipoise at 45 ° C.).

Preparation of Hydroformed Microparticles

Preparations of microparticles were carried out as described in Example I in the different continuous phases except that the propeller speed was 1200–1700 rpm and one baffle was attached to the wall of the beaker.

Analysis of Microparticles

Particle size analysis, SEM, and visual dissolution studies were performed as described in Example 1.

Results

A comparison of microparticles prepared with different viscosity continuous phase media, under similar conditions, showed that when the preparation was made using the higher viscosity mediums (corn oil at room temperature and corn oil heated to 45 ° C.) the product consisted of microparticles that appeared solid, with some chunky domains and plate-like crystals on the surface. Microparticles made in the heated corn oil did show an increase in weight percent of particles less than 150 μm (70%). These microparticles dissolved in 2 days.

The microparticles made using isopropyl myristate were more than 50% by weight larger than 150 µm. These microparticles were comprised of very fine crystals, irregularly packed and easily broken from the microparticle mass. The microparticles dissolve within one day.

The use of methylene chloride as the hydrophobic phase initially produced very small particles, but these agglomerated so that the yield consisted almost entirely of very large clumps or agglomerates of very small particles. The microparticles are composed of loosely packed very fine particles. These microparticles dissolve in less than one day.

As the above discussion demonstrates, a viscous continuous phase advantageously allows the formation of useful microparticles when compared to an essentially non viscous phase, i.e. viscosity less than 5 centipoise. Continuous phase media having a viscosity greater than 10 centipoise produced useful microparticles while higher viscosity media (approximately 25 to 45 centipoise, and preferably greater than 60 centipoise) allowed the formation of well formed and longer lasting microparticles. Useful viscosities in the present invention exist at greater than 5 centipoise and preferably range between about 10 to 100 centipoise, more preferably from 25 to 80 centipoise and even more preferably from about 45 to 60 centipoise.

EXAMPLE III

Effect of Propeller Speed on Microparticle Size Distribution

A parameter which significantly influences size distribution of the microparticle batch is stirring speed of the emulsion.

Preparation of Microparticles

Five batches of hydroformed calcium sulfate microparticles were prepared as described in Example I, batch 1, except that the temperature was 45° C. and the stirring speed was different in each batch. Speeds ranged from 1,200 rpm to 2,200 rpm. Microparticle size was analyzed as described in Example I.

Results

Table 2 below summarizes the effect of varying stirring speed on microparticle size distribution.

| Batch # | Propeller Speed (rpm) | %53–150 µm | % >105 µm |
|---|---|---|---|
| 1 | 1200 | 2 | 97 |
| 2 | 1500 | 10 | 83 |
| 3 | 1700 | 50 | 33 |
| 4 | 1800 | 31 | 12 |
| 5 | 2200 | 25 | 6 |

As stirring speed is increased from 1,200 rpm to 2,200 rpm, the weight percent of microparticles below 105 µm in diameter increased while the weight percent of microparticles above 105 µm decreased simultaneously. Microparticles in the range 53–150µm were obtained in maximum yield at a stirring speed of about 1,700 rpm.

EXAMPLE IV

Hydroformed Calcium Phosphate Microparticles

Microparticles were produced from various calcium phosphate compounds using the novel emulsion method according to the teachings of the present invention. In a first example using hydroxyapatite, equimolar quantities of $CaHPO_4 \cdot 2H_2O$ (1.60 grams) and $Ca_4(PO_4)_2O$ (3.40 grams) were first intimately blended as fine powders by mechanical shaking in a closed vial. 700 ml of corn oil was placed into a 1 liter beaker fitted with a vertical paddle stirrer and stirred at 1950 rpm. The calcium phosphate mixture was then blended by hand with 3.00 ml of water, using a spatula, until a smooth slurry was obtained. The slurry was then transferred, in portions, into the beaker of stirred corn oil, where it was emulsified into a suspension of microparticles. The emulsion was then stirred for about thirty minutes whereupon the speed of the blender was reduced to 1000 rpm. Stirring was then maintained for another 95 minutes at which time the stirring was stopped, hardened microparticles were removed from the corn oil, washed with hexane to remove residual oil, collected by sieving, washed with more hexane, and then air dried. The microparticles were well formed and appeared under a microscope to be composed of microscopic interlocking crystals. The total yield of microparticles was 84%, and of the recovered microparticles, 12% were less than 140 microns in diameter, 55% were between 140–700 microns, and 33% were larger then 700 microns.

In a second example, using dahllite (carbonated apatite), 18 mg of $Ca(H_2PO_4)_2 \cdot H_2O$, 170 mg of $CaCO_3$, 196 mg of $Na_2HPO_4$, and 6.720 gm of alpha-$Ca_3(PO_4)_2$ were ground into an impalpable powder, collected, blended to insure homogeniety, and ground a second time. 2.35 gm of the resulting powder was blended with 650 mg of water to produce a soft putty which was transferred, in portions, into a 600 ml beaker containing 350 ml of corn oil which was then stirred at 890 rpm for 15 minutes. The speed was then reduced to 450 rpm for an additional 4 hours at which time the stirring was stopped, hardened microparticles were removed from the corn oil, washed with hexane to remove residual oil, collected by sieving, washed with more hexane, and then air dried.

EXAMPLE V

Hydroformed Calcium Silicate Microparticles

Commercial Portland cement powder can be employed in the method of Example I to prepare calcium silicate microparticles, however a purified grade of cement can be prepared by calcining mixtures of pure $CaSiO_3$ and $CaCO_3$.

When using a calcined calcium silicate powder, however, it is necessary to modify the method of Example I by replacing the hydrolyzed vegetable oil by an inert mineral oil due to the high alkalinity of the calcium silicate slurry. Additionally, the high alkalinity of the calcium silicate microparticles requires washing of the microparticles with water to neutral pH prior to "post-loading" of any biologically active agent if the chosen agent is sensitive to high pH.

EXAMPLE VI

Preparation of Calcium Sulfate Microparticles Containing Portland Cement

Microparticles were prepared according to the method of Example I, batch 1 except that 4.75 g of calcium sulfate hemi-hydrate was mixed with 0.25 g of Portland cement. Water (5 mls) was added and the mixture was stirred to make a slurry, which was added to the oil as previously described. The propeller speed was 1650 rpm.

Measurement of In Vitro Dissolution Rates

Microparticles and microcapsules produced according to the teachings of the present invention were tested to determine dissolution rates as follows. An accurately weighed sample of either microparticles or microcapsules are placed in a fine mesh inert fabric pouch and suspended in 65 ml of distilled water at 37° C. in a shaker bath. The fine mesh pouches have a pore size of 30 μm, which prevents particle loss during sampling and replacement of the elution buffer while allowing direct contact between the sample and the eluting buffer. This significantly reduces boundary layer effects usually present in systems using dialysis bags. At intervals of 1 to 7 days the calcium ion concentration is measured with a calcium ion electrode (Corning 476041), after which the liquid medium is replaced with fresh solution. The sampling times, liquid volume, and initial sample size is adjusted to achieve calcium concentrations appropriate for sensitive electrode measurements and well below saturate. The experiments are normally continued until the microparticles or microcapsules are fully dissolved.

Results

Dissolution of microparticles was determined by measuring calcium ion release. The microparticles containing 5% Portland cement dissolved in five days.

EXAMPLE VII

Loading Of Hydroformed Microparticles

Two alternative methods may be used to load the mineral microparticles of the present invention with an active ingredient, including a biologically active agent. According to a first "post-load" method, hardened mineral microparticles were prepared according to Example I and then impregnated with a drug, either in solution or in a melted form according to procedures well known in the art. If necessary, the microparticles are then either dried by evaporation or immersed in a drug nonsolvent, such as isopropyl alcohol, to precipitate the drug in situ, followed by evaporation.

According to a second "pre-load" method, the drug is blended with the precursor slurry prepared in Example I just before emulsification and cure of the microparticles. It is important to note that water insoluble drugs may be loaded into the slurry in this method, so long as the drug is not soluble in the continuous phase used for emulsification.

EXAMPLE VIII

Microparticles Loaded with Active Ingredients

Calcium Sulfate Microparticles Incorporating Butyrylcholinesterase

Calcium sulfate microparticles containing butyrylcholinesterase as a representative enzyme were prepared by premixing 1 g of the enzyme powder in 8 ml water with 10 g $CaSO_4$ hemihydrate to make a slurry which was then poured into 400 ml of corn oil at room temperature with a propeller speed of 2200 rpm for 30 minutes. The speed was reduced to 1200 rpm for an additional 30 minutes, then the microparticles were isolated and washed as described in Example I.

Results

SEM revealed round, smooth spheres comprised of calcium salt. One hundred percent of the protein content was recovered in prolonged release from the microparticles.

Calcium Phosphate Microparticles Incorporating Vitamin B 12

In a first example using hydroxyapatite, equimolar quantities of $CaHPO_4.2H_2O$ (1.60 grams) and $Ca_4(PO_4)_2O$(3.40 grams) were intimately blended as fine powders by mechanical shaking in a closed vial. 700ml of corn oil was placed into a 1 liter beaker fitted with a vertical paddle stirrer and stirred at 1950 rpm. 5 gm of the calcium phosphate mixture was then blended by hand with 3.50 ml of water in which 350 mg of Vitamin B 12 had been dissolved, using a spatula, until a smooth slurry was obtained. The slurry was then transferred, in portions, into the beaker of stirred corn oil, where it was emulsified into a suspension of microparticles. The emulsion was then stirred for about thirty minutes whereupon the speed of the blender was reduced to 1200 rpm. Stirring was then maintained for an additional 90 minutes at which time the stirring was stopped, hardened microparticles containing Vitamin B 12 were removed from the corn oil, washed with hexane to remove residual oil, collected by sieving, washed with more hexane, and then air dried.

In a second example, using dahllite (carbonated apatite), 18 mg of $Ca(H_2PO_4)_2$. $H_2O$, 170 mg of $CaCO_3$, 196 mg of $Na_2HPO_4$, and 6.720 gm of alpha-$Ca_3(PO_4)_2$ were ground into an impalpable powder, collected, blended to insure homogeneity, and ground a second time. 5.0 gm of the resulting powder was blended with 1.6 ml of water in which 200 mg of Vitamin B 12 had been dissolved to produce a soft putty which was transferred, in portions, into a 1000 ml beaker containing 600 ml of corn oil which was then stirred at 1250 rpm for 15 minutes. The speed was then reduced to 650 rpm and maintained for an additional 3.5 hours at which time the stirring was stopped, hardened microparticles containing Vitamin B 12 were removed from the corn oil, washed with hexane to remove residual oil, collected by sieving, washed with more hexane, and then air dried.

The following Table 3 lists various additional active ingredients which have been incorporated into calcium sulfate mineral microparticles at various percentages.

| Ingredient Encapsulated | Type | Percent Loading |
|---|---|---|
| Bovine Serum Albumin | Protein | 20.00 |
| Bovine Serum Albumin | Protein | 8.00 |
| Horseradish Peroxidase | Enzyme | 7.00 |
| Horseradish Peroxidase | Enzyme | 0.98 |
| Horseradish Peroxidase | Enzyme | 10.00 |
| Horseradish Peroxidase | Enzyme | 9.30 |
| Vancomycin | Antibiotic | 1.56 |
| Vancomycin | Antibiotic | 8.99 |
| Vancomycin | Antibiotic | 1.55 |
| Tobramycin | Antibiotic | 8.70 |
| Ceftriazone | Antibiotic | 3.47 |
| Ceftriazone | Antibiotic | 9.20 |
| Luteinizing Hormone Releasing Hormone | Hormone | 1.68 |
| Luteinizing Hormone Releasing Hormone | Hormone | 1.26 |
| Luteinizing Hormone Releasing Hormone | Hormone | 0.28 |
| Luteinizing Hormone Releasing Hormone | Hormone | 0.98 |
| Luteinizing Hormone Releasing Hormone | Hormone | 1.76 |

EXAMPLE IX

Coating of Hydroformed Microparticles with Lipid or Wax

The exposed inorganic calcium salt surfaces of the microparticles of the present invention are encapsulated to alter the erosion rates, and thereby, the active ingredient delivery rates of the particular mineral microparticles of the present invention. Microparticles which are encapsulated according to the present invention are termed "microcapsules". The microcapsules of the present invention are advantageous in that the coating is preferably biodegradable and/or bioerodible so that the entire microcapsule biodegrades or bioerodes leaving no non biodegradable or non bioerodible component to contaminate the body. For example, by direct observation of individual calcium sulfate microparticles, it was determined that a 400 μm particle will dissolve in weakly agitated distilled water in about 6 hours. However, by encapsulating the calcium sulfate microparticles in other inorganic salts, hydrogels or biodegradable organic coatings, the dissolution rates are advantageously decreased thereby enabling the microparticles to deliver a given drug over a longer period of time, i.e. from hours to days to weeks to months.

One class of organic coatings capable of extending the dissolution and delivery lifetime of the mineral microparticles is provided by simple biodegradable waxes capable of hindering access of water to both the drug and the mineral matrix.

Preparation

Mineral microparticles were prepared with a loading of 10% bovine serum albumin (BSA) as a prototype protein. To extend the delivery lifetime of these microparticles, a purified triglyceride wax commonly used in suppositories was selected. Although most suppository waxes melt below 37° C., Suppocire D™, a commercially available suppository wax, melts above body temperature at 42°–44° C. A solution of Suppocire D™ in cyclohexane was added to a sample of BSA-impregnated microparticles in an open scintillation vial and evaporated under a slow stream of nitrogen to impregnate the microparticles with the wax. This process, which resembles both pan coating and the techniques used to prepare gas chromatograph column packings, is well known in the art.

Measurement of Rate of Drug Delivery

In vitro drug delivery rates were measured as follows. An accurately weighed sample amount of drug-loaded microparticles or microcapsules were placed in a fine mesh inert fabric pouch. The pouches have a pore size of 30 μm which prevents particle loss during sampling and replacement of the elution buffer while allowing direct contact between the sample and the eluting buffer. This significantly reduces boundary layer effects usually present in systems using dialysis bags. The pouches were suspended in pH 7.4 acetate buffer at 37° C. At given time intervals, the pouches were transferred to fresh extraction baths, and the previous solutions were analyzed for drug content. The concentration of the drug in the extraction medium was not allowed to exceed 10% of saturation and the quantity of microparticles is adjusted to provide results within the range of accurate analysis.

Results

Untreated microparticles and wax-coated microparticles were placed in 10 ml volumes of distilled water and shaken on an automatic shaker. Within a few hours the uncoated microparticles dissolved while the coated sample appeared unchanged after 7 days. These wax-coated microparticles were examined to determine the rate of release of BSA. FIG. 1 is a plot of the percentage release of BSA over a 3 week period which shows an initial burst of BSA delivery during the first two days as protein near the surface washes away, the remaining 60% of the protein payload is released almost linearly for the remainder of the period. The uniformity of delivery is good and the extension in time is quite large, since untreated microparticles can dissolve in less than 1 day. Although about 10% wax was used to treat the microparticles, the porosity of the plaster would allow up to about 30% wax, presumably leading to even longer delivery times.

EXAMPLE X

Coating of Hydroformed Microparticles Containing Butyrylcholinesterase

The microparticles containing protein enzyme, described in Example VIII, were first coated with a triglyceride. Suppocire D™ (0.430 g) was dissolved in 10 ml of ethyl acetate. 5 ml of the solution was added to 4.3 g of microparticles which were coated with the wax according to methods well known in the art until most of the solvent had evaporated. Then the last 5 ml of solution was added and the solvent was evaporated with agitation until the microparticles were dry. A 15% coating of 72:25 poly-DL-lactide-co-glycolide (0.620 g) was applied to 3.95 g of the triglyceride coated microparticles by spraying in a fluidized bed system which is a coating system well known in the art.

Results

Dissolution of the coated microparticles was measured by the calcium ion release as described above. Protein enzyme release was measured by the Lowry method which is well known in the art. Reagents were purchased from Sigma Chemical. The calcium ion release and the protein enzyme release were slowed to greater than 40 days as shown in FIG. 2 as compared to uncoated microparticles.

EXAMPLE XI

Coating of Hydroformed Microparticles with Alginate

Alginates are a class of acidic polyglycosides obtained from large marine algae. They form soluble sodium salts, but crosslink into swollen, insoluble hydrogels in the presence of calcium ions. They are commercially available as the water soluble sodium salts, which rapidly re-gel on exposure to even low concentrations of calcium, such as those which exist in the immediate superficial vicinity of a calcium sulfate microparticle.

Preparation

Calcium sulfate microparticles prepared according to the method of Example I were encapsulated with a layer of calcium alginate hydrogel in the following manner. A 1% solution of sodium alginate (Sigma No. A-2158) was prepared, and calcium sulfate microparticles were introduced into the solution and agitated gently for 1 hour. The alginate solution was then replaced several times with distilled water. The resulting particles were observed to be covered with a transparent layer of alginate gel. Alginate coatings should substantially retard the rate of release of large molecules, and might also provide a route to mineral microparticles with useful bioadhesive properties. Alginates are known to adhere well to moist tissue and mucal membranes, and bioadhesive mineral microparticles could find application in oral vaccines which require antigen absorption through intestinal Peyer's patches. Peyer's patches selectively absorb hydrophobic nanoparticles, and hydrophilic bioadhesive microparticles could adhere to intestinal mucosa and continue to release such nanoparticles for a prolonged period of time.

EXAMPLE XII

Coating Hydroformed Microparticles with Zein

Mineral microparticles were prepared according to the method of Example I, batch 1. A sample of 117 mg of microparticles was placed in 3 ml of a 6 mg/ml methanol/water solution of zein, a corn-derived protein. The volume was reduced by evaporation almost to dryness, then 30 ml of distilled water was added to harden the coating. Yellow coated microparticles were obtained.

Result

The coated microparticles were placed in distilled water at room temperature and were visually observed to remain intact for over two weeks.

EXAMPLE XIII

Coating Hydroformed Microparticles with Inorganic Salts

Calcium sulfates are more soluble than calcium phosphates, which in turn are more soluble than calcium silicates. Therefore, encapsulating the calcium sulfate microparticle with a less soluble inorganic salt will decrease the dissolution rate of the microparticle.

Preparation

Calcium sulfate microparticles produced according to the method of Example I were encapsulated with a phosphate shell in the following manner. Calcium sulfate microparticles were exposed to a pH 7.4 aqueous phosphate buffer comprised of 0.60% sodium chloride, 0.11% monopotassium phosphate, 0.46% disodium phosphate at room temperature for as time sufficient for the more soluble sulfate ions to be substituted on the surface of the microparticle by the less soluble phosphate ions, usually between 30 minutes to 24 hours.

Results

SEM revealed that each microparticle developed a microcrystalline calcium phosphate shell encapsulating the microparticle. After encapsulation, it was demonstrated that the calcium sulfate core could be leached out of the calcium phosphate shell by using distilled water.

Experiments were also performed to convert calcium sulfate microparticles into low solubility calcium silicate. Calcium sulfate microparticles were treated for 24 hours with a sodium silicate solution (Sigma No. S-1773) diluted to a silica content of 1%. Extraction with distilled water for 24 hours left an insoluble core of calcium silicate surrounded by 100–200 micron thick layer of silica gel. Another experiment with a sodium silicate solution containing 27% silica produced insoluble white calcium silicate spheres with no visible gel coat.

It is to be understood that the embodiments of the invention which have been described are merely illustrative of some applications of the principles of the present invention. Numerous modifications may be made by those skilled in the art without departing from the true spirit and scope of the invention.

What is claimed is:

1. A method for producing microparticles comprising the steps of,
   (a) mixing an inorganic calcium salt with water to form an inorganic calcium salt slurry,
   (b) combining the inorganic calcium salt slurry with a liquid substantially immiscible therewith,
   (c) mixing the inorganic calcium salt slurry with the liquid to form an emulsion of inorganic calcium salt slurry particles dispersed in the liquid,
   (d) maintaining the emulsion for a period of time sufficient to allow the inorganic calcium salt slurry particles dispersed in the liquid to form hardened microparticles having an exposed surface of the inorganic calcium salt, and
   (e) retrieving the hardened microparticles of the inorganic calcium salt from the liquid.

2. The method of claim 1 wherein the liquid has a viscosity of greater than 5 centipoise.

3. The method of claim 2 wherein the liquid is a member selected from the group consisting of vegetable oils, mineral oils, and mixtures and combinations thereof.

4. The method of claim 1 wherein step (a) further includes mixing an active ingredient with the inorganic calcium salt slurry.

5. The method of claim 4 further comprising the step of encapsulating the microparticles comprising an active ingredient with a biologically acceptable coating subsequent to retrieving the microparticles from the liquid.

6. The method of claim 5 wherein the biologically acceptable coating is a biodegradable or bioerodible coating.

7. The method of claim 6 wherein the biologically acceptable coating is a member selected from the group consisting of inorganic salts of calcium, hydrogels, waxes, biodegradable polymers, and mixtures thereof.

8. The method of claim 4 wherein the active ingredient is an agricultural agent selected from the group consisting of fertilizers, insecticides, paraticides, and the like.

9. The method of claim 3 wherein the active ingredient is a biologically active agent selected from the group consisting of peptide drugs, protein drugs, desensitizing agents, antigens, vaccines, anti-infectives, antibiotics, antimicrobials, antiallergenics, steroidal anti-inflammatory agents, decongestants, miotics, anti-cholinergics, sympathomimetics, sedatives, hypnotics, psychic energizers, tranquilizers, androgenic steroids, estrogens, progestational agents, humoral agents, prostaglandins, analgesics, antispasmodics, antimalarials, antihistamines, cardioactive agents, non-steroidal anti-inflammatory agents, antiparkinsonian agents, antihypertensive agents, β-adrenergic blocking agents, nutritional agents, and benzophenanthridine alkaloids.

10. The method of claim 1 further comprising the step of
   (f) loading an active ingredient into the microparticles.

11. The method of claim 1 wherein the inorganic salt of calcium is a member selected from the group consisting of insoluble and sparingly soluble calcium sulfates, calcium phosphates, calcium silicates, and mixtures and combinations thereof.

12. A method for producing microparticles comprising the steps of,
   (a) mixing calcium sulfates, calcium phosphates, calcium silicates, or mixtures or combinations thereof with water and a biologically active agent to form an inorganic calcium salt slurry,
   (b) combining the inorganic calcium salt slurry with a liquid substantially immiscible therewith and having a viscosity greater than approximately 5 centipoise,
   (c) mixing the inorganic calcium salt slurry with the liquid to form an emulsion of inorganic calcium salt slurry particles dispersed in the liquid,
   (d) maintaining the emulsion for a period of time sufficient to allow the inorganic calcium salt slurry particles dispersed in the liquid to form hardened microparticles having an exposed surface of the inorganic calcium salt, (e) retrieving the hardened microparticles of the inorganic calcium salt from the liquid, and (f) encapsulating the microparticles with a biodegradable or bioerodible coating.

13. The method of claim 12 wherein the biodegradable or bioerodible coating is a member selected from the group consisting of inorganic salts of calcium, hydrogels, waxes, biodegradable polymers, and mixtures thereof.

14. The method of claim 13 wherein the liquid is a member selected from the group consisting of vegetable oils, mineral oils, and mixtures and combinations thereof.

* * * * *